(12) United States Patent
Cornell

(10) Patent No.: US 8,945,237 B2
(45) Date of Patent: Feb. 3, 2015

(54) ADJUSTABLE PROSTHETIC LIMB SOCKET

(75) Inventor: Keith D. Cornell, Plaistow, NH (US)

(73) Assignee: CJ Socket Technologies Inc., Beverly, MA (US)

( * ) Notice: Subject to any disclaimer, the term of this patent is extended or adjusted under 35 U.S.C. 154(b) by 0 days.

(21) Appl. No.: 13/208,846

(22) Filed: Aug. 12, 2011

(65) Prior Publication Data
US 2012/0041567 A1   Feb. 16, 2012

Related U.S. Application Data

(60) Provisional application No. 61/373,258, filed on Aug. 12, 2010.

(51) Int. Cl.
| | |
|---|---|
| *A61F 2/78* | (2006.01) |
| *A61F 2/80* | (2006.01) |
| A61F 2/50 | (2006.01) |
| A61F 2/76 | (2006.01) |

(52) U.S. Cl.
CPC ... *A61F 2/80* (2013.01); *A61F 2/78* (2013.01); A61F 2002/5026 (2013.01); A61F 2002/5027 (2013.01); A61F 2002/5052 (2013.01); A61F 2002/5056 (2013.01); A61F 2/76 (2013.01); A61F 2002/7818 (2013.01); A61F 2002/805 (2013.01); A61F 2002/5053 (2013.01); A61F 2002/7881 (2013.01); A61F 2002/802 (2013.01); A61F 2210/0071 (2013.01)
USPC .................................. 623/33; 623/34; 623/36

(58) Field of Classification Search
USPC .................. 623/32, 33, 34, 35, 36, 37, 38
See application file for complete search history.

(56) References Cited

U.S. PATENT DOCUMENTS

| 366,494 | A | * | 7/1887 | Marks | 623/53 |
|---|---|---|---|---|---|
| 470,431 | A | * | 3/1892 | Marks | 623/33 |
| 1,066,605 | A | * | 7/1913 | Hanger | 623/33 |
| 2,253,040 | A | * | 8/1941 | Martino | 623/36 |
| 2,273,695 | A | * | 2/1942 | Dew | 623/33 |
| 4,634,446 | A | * | 1/1987 | Kristinsson | 623/33 |
| 4,842,608 | A | | 6/1989 | Marx et al. | |
| 5,405,405 | A | * | 4/1995 | Love | 623/37 |
| 5,529,575 | A | * | 6/1996 | Klotz | 623/33 |
| 5,653,766 | A | | 8/1997 | Naser | |
| 5,724,714 | A | | 3/1998 | Love | |
| 5,853,378 | A | | 12/1998 | Modglin | |
| 5,967,998 | A | | 10/1999 | Modglin | |
| 6,213,968 | B1 | | 4/2001 | Heinz et al. | |

(Continued)

FOREIGN PATENT DOCUMENTS

| DE | 102006046928 | 4/2008 |
|---|---|---|
| GB | 107447 | 7/1917 |

*Primary Examiner* — Marcia Watkins
(74) *Attorney, Agent, or Firm* — Antoinette G. Giugliano; AGG Intellectual Property Law

(57) ABSTRACT

The present relates to an adjustable prosthetic limb socket system having a partial rigid support, a non-elastic, flexible support and adjustment means. The adjustable socket system of the present invention can be used for several types of amputations including transfemoral amputations, transtibial amputations, transhumeral amputations, transradial amputations, and other types of amputations. The present invention further includes kits having the adjustable prosthetic limb socket system, as well as methods of making the adjustable prosthetic limb socket system. Methods of using the socket system are further encompassed by the present invention.

23 Claims, 19 Drawing Sheets

(56) References Cited

U.S. PATENT DOCUMENTS

| | | |
|---|---|---|
| 6,322,529 B1 | 11/2001 | Chung |
| 6,508,842 B1 | 1/2003 | Caspers |
| 6,589,289 B2 | 7/2003 | Ingimarsson |
| 6,676,620 B2 | 1/2004 | Schwenn et al. |
| 6,793,682 B1 | 9/2004 | Mantelmacher |
| 7,186,229 B2 | 3/2007 | Schwenn et al. |
| 7,201,727 B2 | 4/2007 | Schwenn et al. |
| 7,306,571 B2 | 12/2007 | Schwenn et al. |
| 7,473,235 B2 | 1/2009 | Schwenn et al. |
| 7,670,386 B2 | 3/2010 | Ezenwa |
| 7,886,618 B2 | 2/2011 | Macomber et al. |
| 2006/0009860 A1 | 1/2006 | Price |
| 2007/0225824 A1 | 9/2007 | Einarsson |
| 2010/0191348 A1* | 7/2010 | Kettwig et al. ............ 623/33 |
| 2010/0274364 A1* | 10/2010 | Pacanowsky et al. ........ 623/36 |

* cited by examiner

ADJUSTABLE PROSTHETIC LIMB SOCKET

RELATED APPLICATIONS

This application claims the benefit of U.S. Provisional Application No. 61/373,258, filed Aug. 12, 2010 entitled, "Adjustable Prosthetic Limb Socket" by Keith D. Cornell.

The entire teachings of the above application(s) are incorporated herein by reference.

BACKGROUND OF THE INVENTION

A prosthetic device for an arm or leg is traditionally worn by inserting the residual limb into a rigid or semi-rigid socket. Traditional sockets are designed as a 360 degree container surrounding the entire residual limb. Sockets generally perform at least two broad functions. Firstly, the traditional socket is designed to allow comfortable weight bearing and prevent soft tissue damage as weight pressures are applied to the residual limb via the prosthetic socket. This is generally achieved with a combination of skeletal weight bearing and hydraulic lift created as the residual limb fluids are pressurized in the socket. Secondly, the traditional socket also functions to stabilize the skeletal components of the residual limb such that the user can move the prosthesis in space and minimize relative motion between the socket and the residual limb.

A precise volumetric fit greatly aids both of these functions. Maintaining a proper amount of volumetric socket fit is challenging and often problematic due to the tendencies of the residual limb to change in volume and the soft tissue to displace under load. Residual limb volume change (RLVC) occurs due to many factors, including but not limited to: edema, muscle atrophy, weight gain/loss, renal dialysis, salt and water intake, alcohol consumption, menses, changes in wearing time and activity. Residual limbs also loose volume daily due to socket pressure and the pumping action of ambulation. Daily volume loss is generally replenished during non-wearing times i.e. sleep, and is cyclical and greatly affected by activity.

As the residual limb loses volume the hydrostatic weight bearing and skeletal control characteristics of the socket are compromised. This leads to painful, limiting and/or injurious increases in socket pressure as well as energy wasting and destabilizing excessive motion between the socket and skeletal segments of the residual limb. As the user attempts to control the prosthesis in space by employing their proximal musculature, relative motion between the residual limb and prosthesis causes forces which accelerate and impact the residual limb. These forces can be compressive, or cause strain or shear, which in turn increase localized pressure and/or tension on the residual limb. This commonly results in pain and injury as well as increased energy use and premature fatigue. As a result, traditional sockets tend not to function well when changes in the residual limb's volume, shape or size occur. This is a common occurrence and has not been addressed effectively.

Additionally, residual limbs are often bulbous in shape with the distal dimensions larger than those more proximal. This shape can cause difficulty in donning the socket because the socket pushes past the larger distal dimension to be secured to the smaller proximal socket dimension Accordingly, a need exists for a prosthetic limb socket that maintains a proper volumetric fit despite significant volume changes and reduces unwanted relative motion between the residual limb and the prosthesis. Accordingly a need exits for sockets to accommodate bulbous shaped residual limbs.

SUMMARY OF THE INVENTION

The present invention relates to a socket for the attachment of a prosthetic device to the residual limb (RL) of an individual, the residual limb having a circumference, surface area and volume. The socket includes a rigid support (typically J shaped), wherein the rigid support is shaped to conform to at least a portion of the residual limb, the rigid support having rigid member e.g., extending along the long axis of the RL and a distal base. The socket also includes a non-elastic, flexible support (e.g., a flexible garment) referred to herein as a "sail" secured to the rigid support; and an adjustable means to maintain a volumetric fit of the residual limb, wherein the adjustable means is attached to the rigid support, the non-elastic flexible support, or both, and wherein the adjustable means provides an adjustable circumferential force to obtain a volumetric fit. The socket of the present invention, in certain embodiments, also has an attachment for a prosthetic device wherein the attachment is at the distal base of the rigid support. The rigid member is shaped to conform to at least about 15% of the surface area of the residual limb (e.g., between about 10% to about 75% of the surface area). In an embodiment, the rigid member is shaped to conform to at least about 50% of the surface area of the residual limb. In another aspect, the rigid member is shaped to cover between about 54° and about 270° of the circumference of the residual limb. The socket of the present invention includes e.g., a gel liner, a locking mechanism or other means such as a vacuum port or belt to suspend the socket or hold the socket onto the residual limb.

The present invention further relates to a socket for the attachment of a prosthetic device to a residual limb of an individual, the residual limb having a circumference, volume and a surface area, wherein the socket has a rigid support, wherein the rigid support includes a distal base and a rigid member that is shaped to conform to at least a portion of the residual limb wherein the rigid member covers at least about 180° of the circumference of the residual limb, thereby leaving a balance of the residual limb unsupported by the rigid support. The socket also includes a flexible support (e.g., sail), secured to the rigid support, wherein the flexible support covers most or all of the balance of the residual limb and wherein the flexible support is made from a flexible non-elastic material; and an adjustable means to maintain a volumetric fit of the residual limb, wherein the adjustment means are attached to the rigid support, the non-elastic flexible support, or both; and wherein the adjustment means adjusts to fit the circumference of the residual limb and provide circumferential and lift forces; and an attachment for a prosthetic device, wherein the attachment is at the distal base of the rigid support. The rigid support can be made from a material that includes thermoplastics such as polypropylene and copolymers, or laminations of acrylic, polyester or epoxy resins layered with nylons, carbon braids or fiberglass cloths or a combination thereof.

The present invention embodies methods of using the socket described herein. The methods involve a prosthetic device that is attached to the socket and the socket is secured to a residual limb of an individual; the steps of the method simply include using the prosthetic device (e.g., walking, running, lifting, or jumping with the prosthetic device). The methods of the present invention also pertain to the steps of applying the socket over the residual limb, wherein the rigid support is positioned to conform to the residual limb; and engaging the adjustment means to fit the circumference of the residual limb and provide circumferential forces. In particular, the methods can include applying an initial gel liner to the residual limb before applying the socket; applying a second gel liner over the socket such that the second gel liner meets the initial gel liner; and vacuum sealing the socket. In the case of a locking gel liner, the methods include the steps of applying a locking gel liner to the residual limb before applying the socket; and engaging a mechanical lock with a locking liner.

The present invention also relates to a method of making the socket described herein. The steps of making the socket of the present invention include measuring the residual limb; making a mold that conforms to a residual limb; making a rigid support that covers and conforms to at least 15% of the surface area of the residual limb, thereby leaving a balance of the residual limb not covered by the rigid support; and attaching a flexible support (e.g., sail) that covers the balance of the residual limb, wherein the flexible support includes the adjustment means to provide volume adjustability in the system. The rigid support can be made from a material that comprises thermoplastics such as polypropylene and copolymers, or laminations of acrylic, polyester or epoxy resins layered with nylons, carbon braids or fiberglass cloths or a combination thereof. The flexible support can be made of a non-elastic textile fabric, a polyamide, an aramid, para-aramid synthetic fiber, or a combination thereof The present invention further embodiment kits. A kit of the present invention includes a non-elastic, flexible support; an adjustment means to maintain a volumetric fit of the residual limb, and a rigid support. Additional items of the kit include items described herein, those that are useful in making or adjusting the socket of the present invention. Examples include one or more gel liners, a locking mechanism, a vacuum port, suspension belt and the like.

The present invention also relates to the rigid support for use with socket for the attachment of a prosthetic device to a residual limb of an individual. The rigid support has e.g., a distal base, wherein the distal base receives a distal end of the residual limb; and a rigid member that is shaped to conform to at least a portion of the residual limb wherein the rigid member covers between about 36° and about 270° of the circumference of the residual limb or between about 10% and 60% of the surface area of the residual limb.

The present invention has a number of advantages over traditional sockets. The socket of the present invention provides comfortable weight bearing and adequate stability to control the prosthesis in space. Volume control of the socket of the present invention is unprecedented using the adjustable flexible support or garment.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

The present invention relates to a new socket design that is stable, comfortable, and allows for volumetric changes in the residual limb. In particular, the present invention relates to a socket that has a rigid support that conforms to a portion of the residual limb, and a sail (also referred to herein as a "flexible support") which is a strong, flexible and preferably non-elastic garment that covers the balance of the circumference of the residual limb. The socket system of the present invention also includes a means for securing the sail e.g. with a closure system, and an attachment at the base of the rigid support for attaching the prosthetic device.

Unlike traditional sockets that include a rigid or semi-rigid socket that conforms to most or all of the outer circumference of the residual limb, the rigid support of the present invention is a partial support. More specifically, in an aspect, the rigid support of the present invention covers only about 50% or more of the surface area of the residual limb, or about 180° or more of the circumference of the residual limb. Having a rigid socket that covers only a portion of the residual limb is counter to traditional practices. Traditional prosthetic devices generally involve applications in which rigid or semi-rigid support covers most of the circumference of the residual limb. Accordingly, the present invention including only a partial rigid support in a socket that provides support, comfort and adjusts for volumetric changes is unprecedented, surprising and unexpected. As defined herein, the term "socket" or "socket system" refers to the combination of the rigid support and the sail (e.g., flexible support). Additionally, the term "J-socket" refers to the rigid support that is shaped as a "J" as further described herein.

Since the new socket design of the present invention, shown in the Exemplification, only covers about half or 180° of the residual limb with conventional rigid or semi-rigid materials, the exposed area is controlled by an integrated non-elastic flexible, yet strong garment, referred to herein as a "sail" or "flexible support" which secures the residual limb to the rigid support and affords 360° of control. By eliminating about half of the rigid socket, the sail can then adjust the circumference of the socket to accommodate even moderate volume changes maintaining optimum fit and control of the prosthesis.

Figure 1:
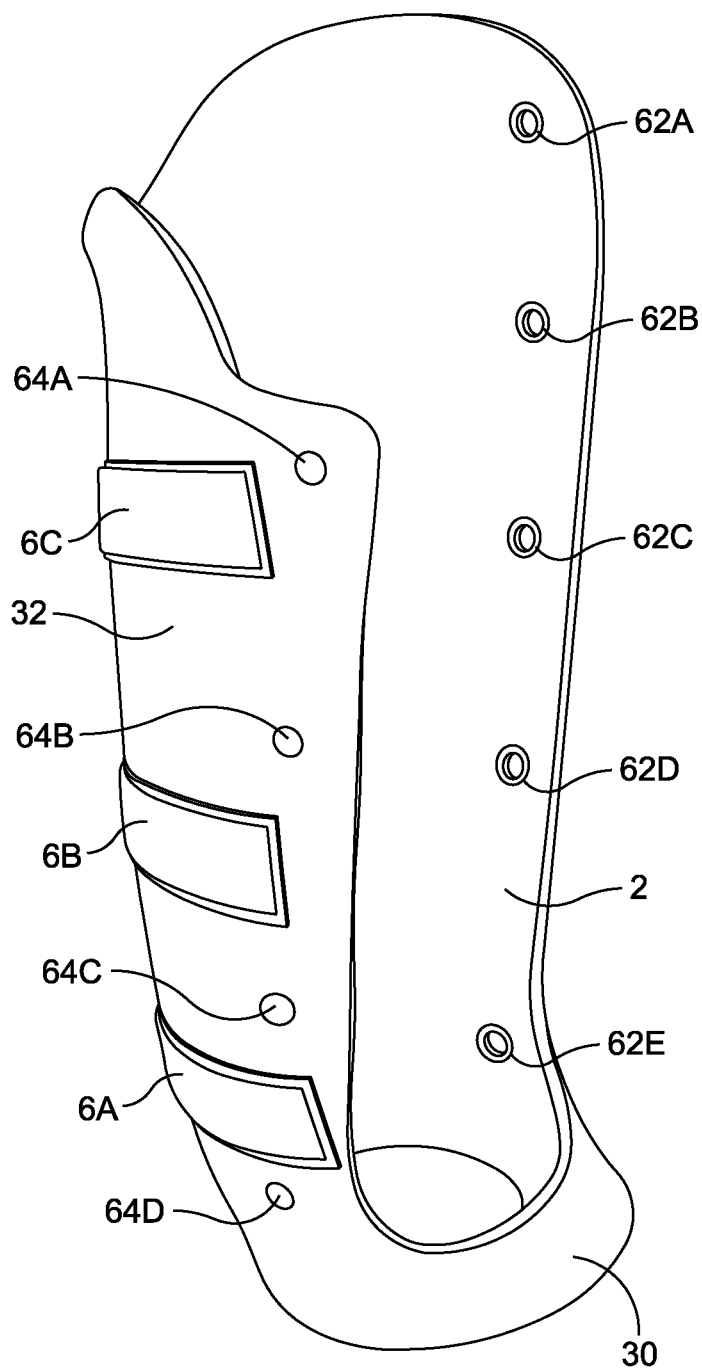
FIG. 1 is a schematic drawing showing a perspective view of the rigid support (e.g., "J-socket") of the "transfemoral posterior sail socket" of the present invention without the posterior flexible support (e.g., the posterior sail).
Figure 2A:
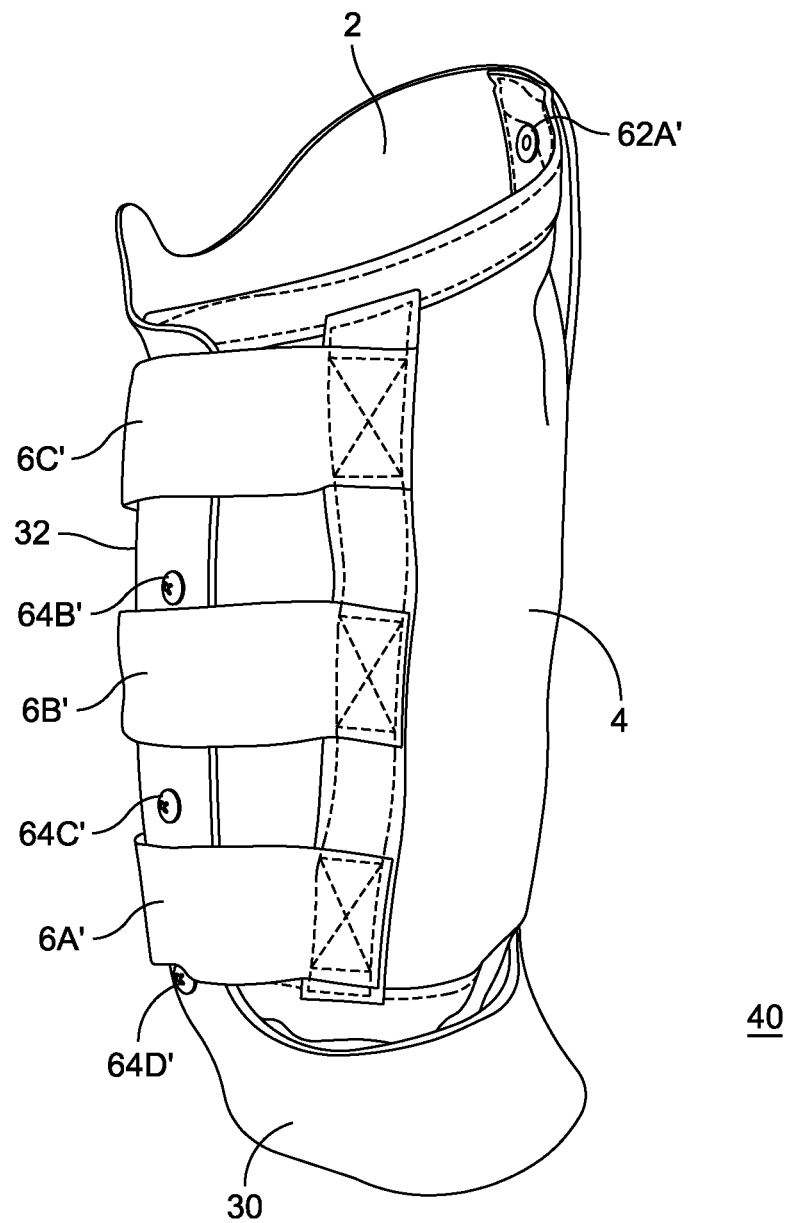
FIG. 2A is a schematic drawing showing a perspective view of the rigid support of the transfemoral posterior sail socket of the present invention with the posterior flexible support and adjustment means.

With respect to FIG. 1, rigid support 2 of socket system 40 (as shown in FIG. 2A) is made from a moldable material that hardens to conform to the contours of the residual limb. Socket 40 is made for a leg that was amputated above the knee, a transfemoral amputation. The socket of the present invention can be used for any type of amputation including those that occur above (e.g., transfemoral) or below (e.g., transtibial) the knee, or those that occur above (e.g., transhumeral) or below (e.g., transradial) the elbow. The present invention can be used for other type of amputations including those of the foot, ankle, hand or wrist. For example, the present invention can be used for Symes, Lis franc and Chopart partial foot amputations and wrist disarticulations.

Rigid support 2 is an example of a J-socket that is used in a transfemoral posterior sail socket system. Another type of transfemoral socket system of the present invention is a transfemoral anterior sail socket system (see FIGS. 5-9). An anterior sail socket system is often used on an individual that does not use weight bearing ambulatory aids such as crutches or walkers. In practice, the transfemoral posterior sail socket system is used for all other patients because the posterior sail is more comfortable while the individual is in a sitting position.

With respect to the transfemoral socket systems, both anterior and posterior sail systems provide an additional advantage. Traditional transfemoral sockets specifically are problematic due the relatively fixed proximal anterior/posterior (AP) diameter, the diameter of the residual limb measured from the anterior side to the posterior side of the limb. When sitting, the thigh soft tissues normally splay or spread thereby significantly reducing the AP diameter. This is essential to allow sufficient hip flexion required e.g., when one bends over to tie a shoe or reach something on the floor. Traditional rigid or semi-rigid transfemoral sockets do not splay in sitting resulting in discomfort and significant restriction in hip flexion making activities which require bending to reach the floor difficult. The present invention solves this problem with the use of a combination of a partial rigid support and a flexible sail.

Rigid support 2 of FIG. 1 covers about 180° of the circumference of the residual limb or about 50% of the surface area of the residual limb. The circumference of a residual limb refers to the outside distance around the limb starting and ending at the same point. The residual limb is often not perfectly symmetrical and can have irregular areas, and so the measurement of the circumference includes the distance around limbs that may or may not be symmetrical. Rigid support 2 has distal base 30 continuous with rigid member 32. A side view of the rigid support shows that it forms a "J" shape and is referred to herein as a "J-socket". This unique shape, together with the flexible garment, allows for a comfortable socket system providing a volumetric fit for the individual. The rigid support of the present invention includes the rigid member that covers between about 54° and 270° (e.g., about 60°, 70°, 80°, 90°, 100°, 110°, 120°, 130°, 140°, 150°, 160°, 170°, 180°, 190°, 200°, 210°, 220°,230°, 240°, 250°, 260°, and 270°) of the circumference of a residual limb, and preferably about 180° of the circumference of the limb. In another embodiment, the rigid support of the present invention conforms to the residual limb and covers between 15% to about 75% of the surface area of the residual limb, and preferably about 50%. Having a rigid support that conforms to only a portion (e.g., about half) of the limb provides comfort to the individual, as compared to a fully rigid socket covering most or all of the limb's circumference and/or surface area. The base of the rigid support conforms to receive the distal end of the residual limb and in an embodiment, covers the entire distal limb or 360° of the distal limb. In the preferred embodiment, the rigid support and base are continuous, however, the two parts can be present and in communication with one another in any way so long as the proper support and stability are provided.

In an embodiment, the rigid support or the J-socket is made from a molding process, described herein. This process allows the rigid support to conform to the shape of a portion of the residual limb. The rigid support can be trimmed and/or tapered as desired. The rigid support can conform to any portion of the residual limb, but can run most or all of the length of the residual limb. In a preferred embodiment for lower function level transfemoral amputees, the rigid support conforms to the anterior and lateral portions of the limb. In this case, the posterior and medial portion of the residual limb is covered by the flexible support of the socket, which is further described herein. For amputations through the femur, this embodiment of the socket allows more comfort to the individual when sitting and wearing certain types of clothing. Since the posterior portion of the leg limb is supported by the flexible support of the socket, there is minimal interference between the socket and the sitting surface thereby allowing the individual's prosthetic limb to sit similarly to the non-amputated leg. In a particular embodiment, the rigid supports trim line was established as follows: the trim line begins posterior to the adductor longus tendon origin and then inferiorly to a point approximately 2 inches proximal to the distal end, then extending posteriorly (roughly) 180° and then proximally to posterior lateral apex, just posterior to the Greater Trochanter in the area often referred to as the wallet hollow. Although the present invention includes a rigid support conforming to the anterior and lateral portions of the limb, the rigid support can conform to one or more of any surface or side of the limb including anterior side, lateral side, posterior side, medial side or any combination thereof.

Figure 2B:
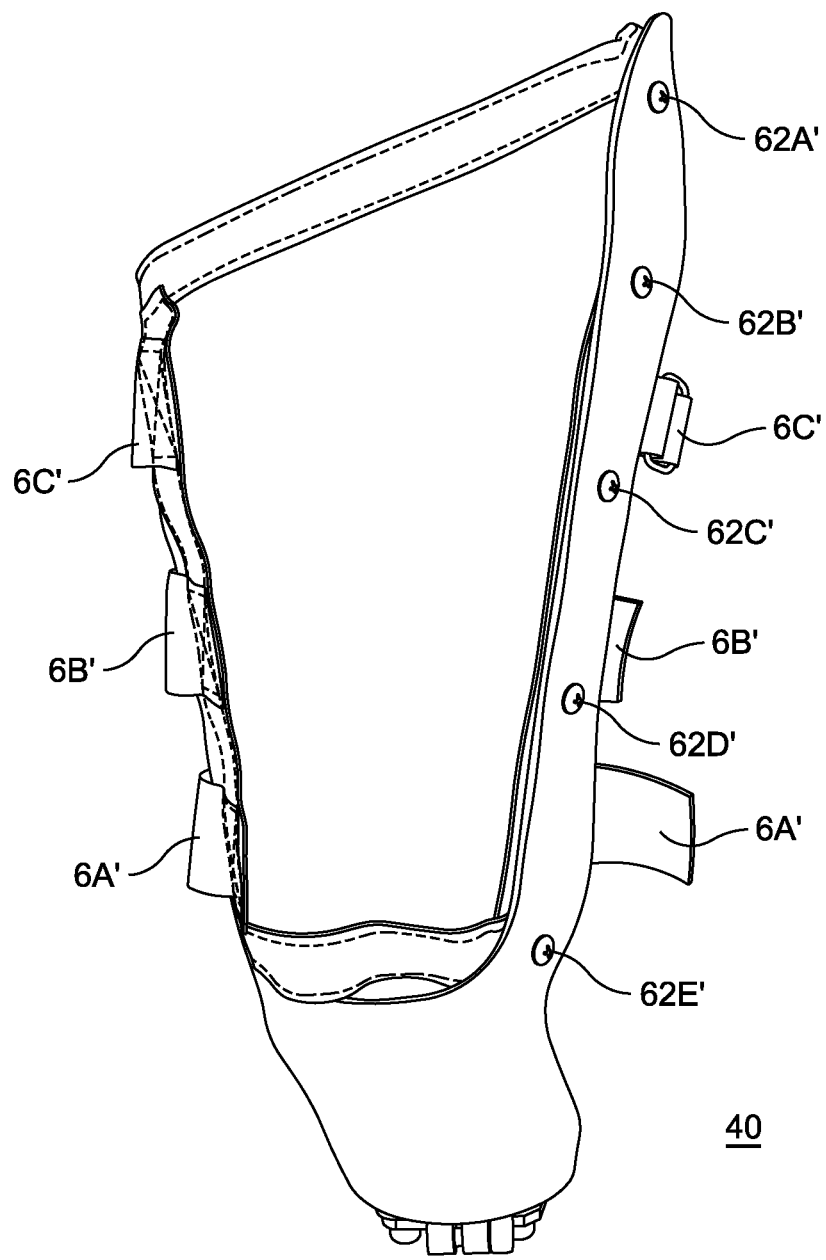
FIG. 2B is a schematic drawing showing a posterior view of the rigid support of the transfemoral posterior sail socket of the present invention with the posterior flexible support and adjustment means.
Figure 3:
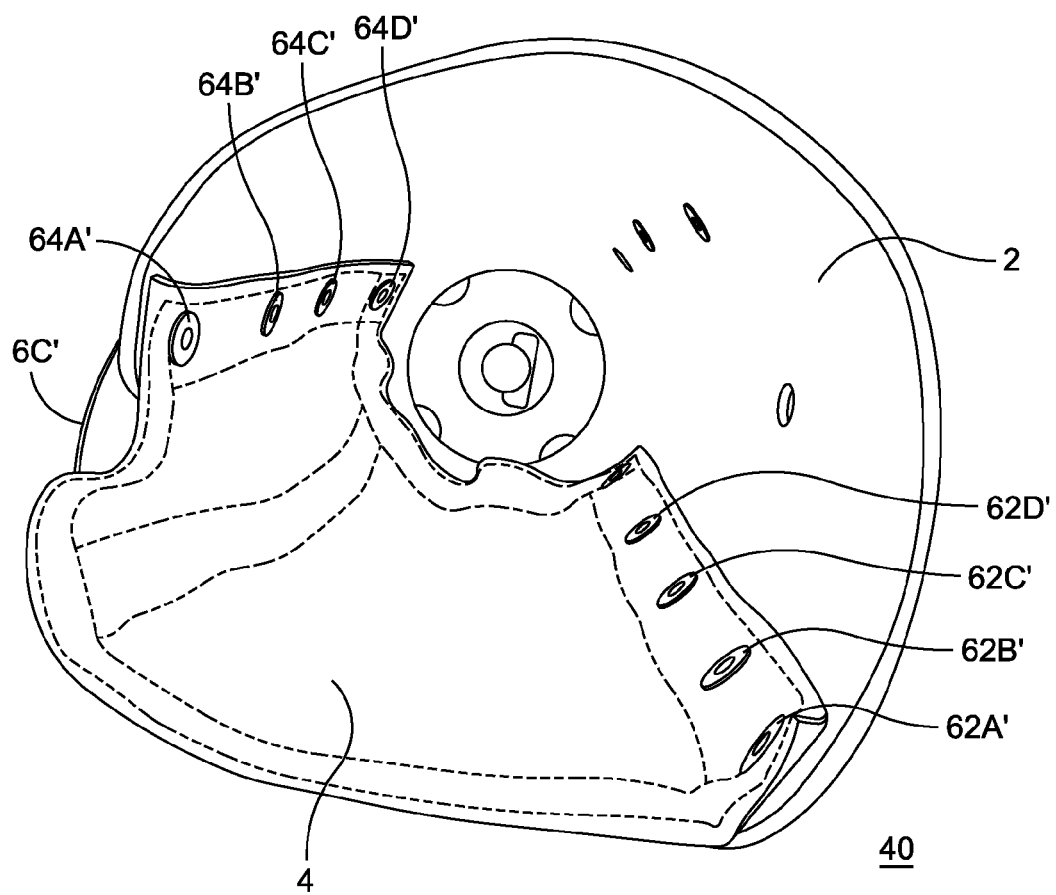
FIG. 3 is a schematic drawing showing a top view of the rigid support of the transfemoral posterior sail socket of the present invention with the posterior flexible support.

FIGS. 2A-2B, and 3 show socket system 40 of the present invention with the sail or flexible support 4. In FIGS. 2A and 2B, flexible support 4 is shown and secured to one of the sides of the rigid support with grommets $62A^1$, $62B^1$, $62C^1$, $62D^1$, and $62E^1$ that correspond with openings 62A, 62B, 62C, and 62D in rigid support 2 (see FIG. 1). The other side of flexible support 4 is also attached with grommets $64A^1$-$D^1$ that correspond with openings 64A-D. See FIG. 3. The flexible support can be attached or secured (e.g., with securing means) to the rigid support in any way known in the art. Examples of securing means that can be used with the present invention include snaps, buckles, buttons, rivets, hooks (e.g., hook-to-hook arrangements hook & loop arrangements, snap hooks), elastic members, key-lock arrangement, ties, clips, zippers, hook & loop arrangements, magnets, adhesive, and combinations thereof. Combinations of one or more of such items can be used as an attachment means. Securing means that are now known or later developed can be used so long as the fastener allows the flexible support to be attached to the rigid support. Fasteners are commercially available, and can be obtained, for example from National Webbing Products Co. (Garden City Park, N.Y.), or National Molding Corporation (Farmingdale, N.Y.).

The flexible support, in an embodiment, is essentially a non-elastic, strong, non-rigid support. The sail by itself can be seen in FIG. 4. The flexible support is preferably a garment. The width and height of the flexible support will depend on the size of the residual limb, the size of the rigid support, and the location of the amputation (e.g., transtibial, transfemoral, transhumeral, or transradial). The width and/or height of the flexible support are sufficient to allow both the flexible and rigid supports to surround most or all of the circumference of the residual limb.

As shown in FIGS. 2A and 2B, the width of the sail can extend from one side of the rigid support to the other side. In an alternative embodiment, the sail can be wrapped around the entire circumference, including the rigid support, of the residual limb. In a particular embodiment described in the Exemplification, the width of the garment for the socket system shown in FIGS. 2A and 2B was determined by a tapeline measurement, measuring from the posterior lateral socket trim line to anterior medial socket trim line. The length of the garment was measured from the gluteal fold to the bottom of the socket trim line.

In a particular embodiment the sail measurements for transtibial J-socket (e.g., rigid support) is determined with tapeline measurements measuring from the posterior lateral socket trim line posterior to the fibula head and extending horizontally posteriorly and medially to the posterior medial tibia. A second measurement is made from the posterior mid-level of the fibula extending horizontally posteriorly and medially to the mid-level of the tibia and a third horizontal measurement is made in the same directions at the distal trim lines. The length of the garment is measured from the proximal posterior trim line to the distal base medially and laterally.

In a particular embodiment the sail measurements for a transhumeral J-socket is determined with tapeline measurements measuring horizontally from the proximal posterior auxiliary trim line to the anterior proximal auxiliary trim line. A second measurement is made from the distal posterior trim line to the anterior distal trim line. The length is measured from the posterior and anterior proximal trim lines to the distal base.

In a particular embodiment the sail measurements for transradial J-socket is determined with tapeline measurements measuring horizontally from the proximal posterior trim line to the anterior proximal trim line. A second measurement is made from the distal posterior trim line to the anterior distal trim line. The length is measured from the posterior and anterior proximal trim lines to the distal base.

Figure 4:
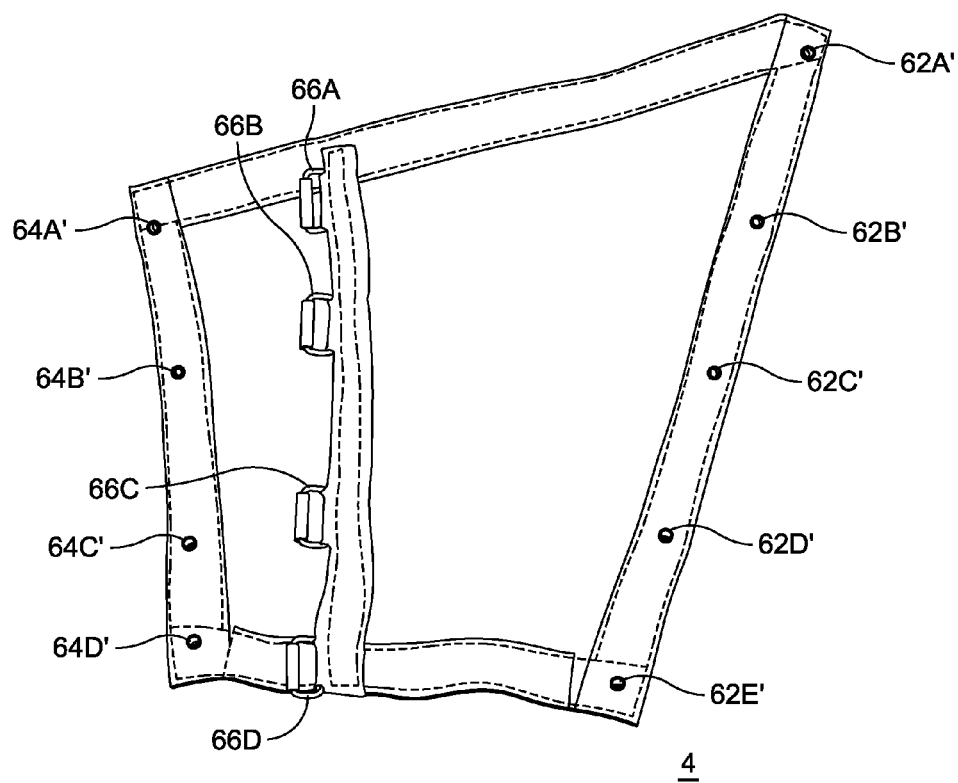
FIG. 4 is a schematic drawing showing a side view of the flexible support (e.g., the sail) of the socket of the present invention of the transfemoral socket.

In an aspect, the height of the flexible support ranges between about 3 inches to about 14 inches, and the width ranges between about 6 inches to about 14 inches. The flexible support can come in various sizes (e.g., small, medium, large; tapered or standard; a set of sizes such as 0-10, or be custom fabricated). The sizing system can be assessed and based on the type of limb, type of amputation, size of limb, size of rigid support and the like. As can be seen in FIG. 4, the sail is shaped to correspond with the shape of the residual limb. In particular, the edges (e.g., the top seam) can angled, trimmed, or cut to accommodate the shape of the residual limb. Accordingly, the sail can have an irregular shape, or can be essentially a rectangular shape.

The flexible support can further include attachments to which the adjust means can be used or secured. For example, FIG. 4 shows rings 66A-66D through which the loop fasteners (e.g., VELCRO® fasteners) pass to be secured and to collapse the width of the sail to fit the circumference of the residual limb.

Although flexible, the flexible support should be strong enough to withstand the force of securing the socket to the limb, and the force using the prosthetic device. The flexible support can be made from a non-elastic flexible material. Materials for the flexible support can be a non-elastic textile fabric, a synthetic polymer such as a polyamide, an aramid or para-aramid synthetic fiber. Examples of synthetic polymers include nylon, and KEVLAR® synthetic fiber. The tensile strength of nylon ranges from about 45 MPa to about 75 MPa, and the specific strength ranges of about 69 kN·m/kg. The tensile strength of KEVLAR® synthetic material is about 3620 MPa, and its specific strength ranges is about 2,514 kN·m/kg. Tensile strength generally refers to a measurement of the maximum amount of force a material can withstand before tearing or breaking. The specific strength is a material's strength (force per unit area at failure) divided by its density, or a strength to weigh ratio. Any flexible, lightweight material can be used so long as the material has a tensile strength (e.g., between about 40 and about 4000 MPa) and/or a specific strength (e.g., about 50 kN·m/kg to about 3000 kN·m/kg) to withstand the force of the use of the prosthetic device including force to maintain stability and weight bearing. Both Nylon 6-6 fabric and KEVLAR® synthetic fibers are commercially available from DuPont (Wilmington, Del.).

Flexible support adjusts to fit the circumference of the residual limb and secure the socket to the limb. The flexible support can be tightened or bunched to reduce the circumference of the overall socket to fit the circumference of the residual limb, as shown in FIGS. 2A and 2B. An adjustment mean can be used to adjust the flexible support to fit the circumference. In the embodiment shown in FIGS. 1-4, a closure system including hook and loop fasteners were used to adjust the flexible support. FIG. 1 shows hook fasteners 6A, 6B and 6C attached to rigid support 2. FIG. 2A shows loop fasteners $6A^1$, $6B^1$ and $6C^1$ which are attached to the flexible support 4. Flexible support 4 is adjusted by fastening the loop fasteners to the hook fasteners e.g. through a ring attached to the sail. The adjustment means collapses the width garment to decrease the overall circumference of the socket and apply circumferential forces to the residual limb (See FIG. 2A).

The adjusting means applies circumferential force to maintain proper hydrostatic weight bearing and accommodating RLVC. In an embodiment, applying circumferential forces to fit the volume of the limb allows the socket proper weight bearing and skeletal control to remain during walking, running or general use of the prosthesis. In an aspect, the adjusting means allows for the overall circumference of the socket to be adjusted as volumetric changes in the residual limb occur. The closure can be tightened or loosed depending on the comfort and stability of the prosthetic device. For example, the adjusting means can employ fasteners, straps, snaps, buckles (e.g., cam buckles or center release buckles), buttons, hooks (e.g., hook-to-hook arrangements, hook & loop arrangements, snap hooks), elastic members, trap-locks (e.g., plastic trap-locks), ties, laces, clips, zippers, metal loops or roller loops, drawstring & cord lock arrangements, hook-to-hook arrangements, hook & loop arrangements, bungee cord & cord lock arrangements, magnets, slides (e.g., plastic slides), block and tackle arrangements, rope/chord and hook arrangements, combinations thereof and the like.

Optionally, to prevent the garment from slipping or riding down and thereby not sufficiently encapsulating the necessary soft tissues, one or more additional mounts or hooks can be added at the top of the rigid support, through which a strap or cord can be passed.

FIG. 3 is a top view of the socket of the present invention. From this view, the flexible support is mounted to the outside surface of the rigid support. It can also be seen that the rigid support conforms to the shape of the residual limb, whereas the flexible support does not until it is secured to the limb.

Figure 5:
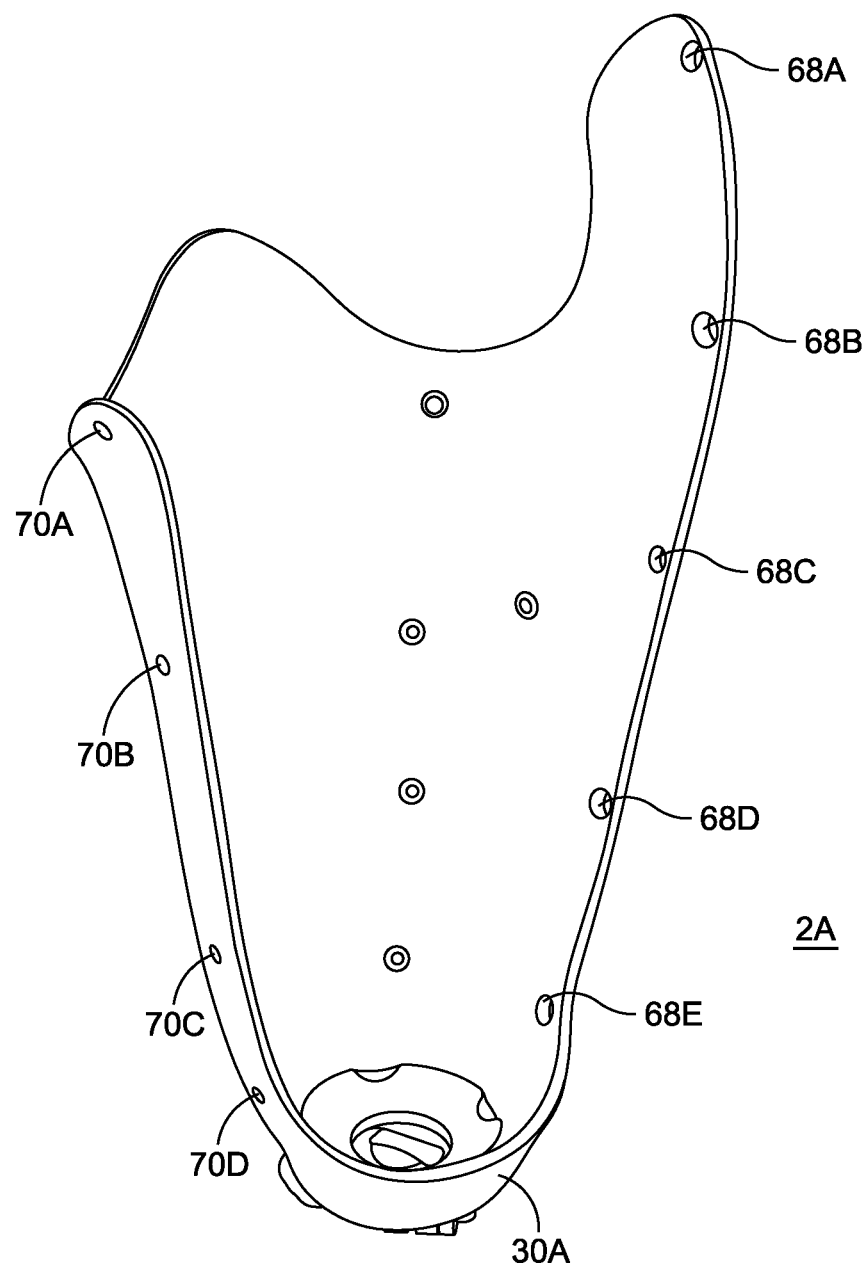
FIG. 5 is a schematic showing an anterior view of the rigid support (e.g., "J-socket") of the transfemoral anterior sail socket of the present invention without the anterior flexible support (e.g., anterior sail).

FIG. 5 shows rigid support 2A is another example of a J-socket. Rigid support 2A has base 30A and rigid member 32A to form a "J" shape. As described herein, the base covers essentially all of the distal portion of the residual limb and the rigid member conforms to a portion of a side of a limb, in this case the posterior side of the limb. The rigid support is to be used in a transfemoral anterior sail socket, so the rigid member of the rigid support conforms to the posterior side of the residual femoral limb. The proximal portions of the J-socket, as compared to that of the transfemoral posterior sail socket system, differ and extend to support different anatomical structures. Methods of making sockets are known in the art and can be adapted to making the J-socket shown in any of the figures.

Figure 6A:
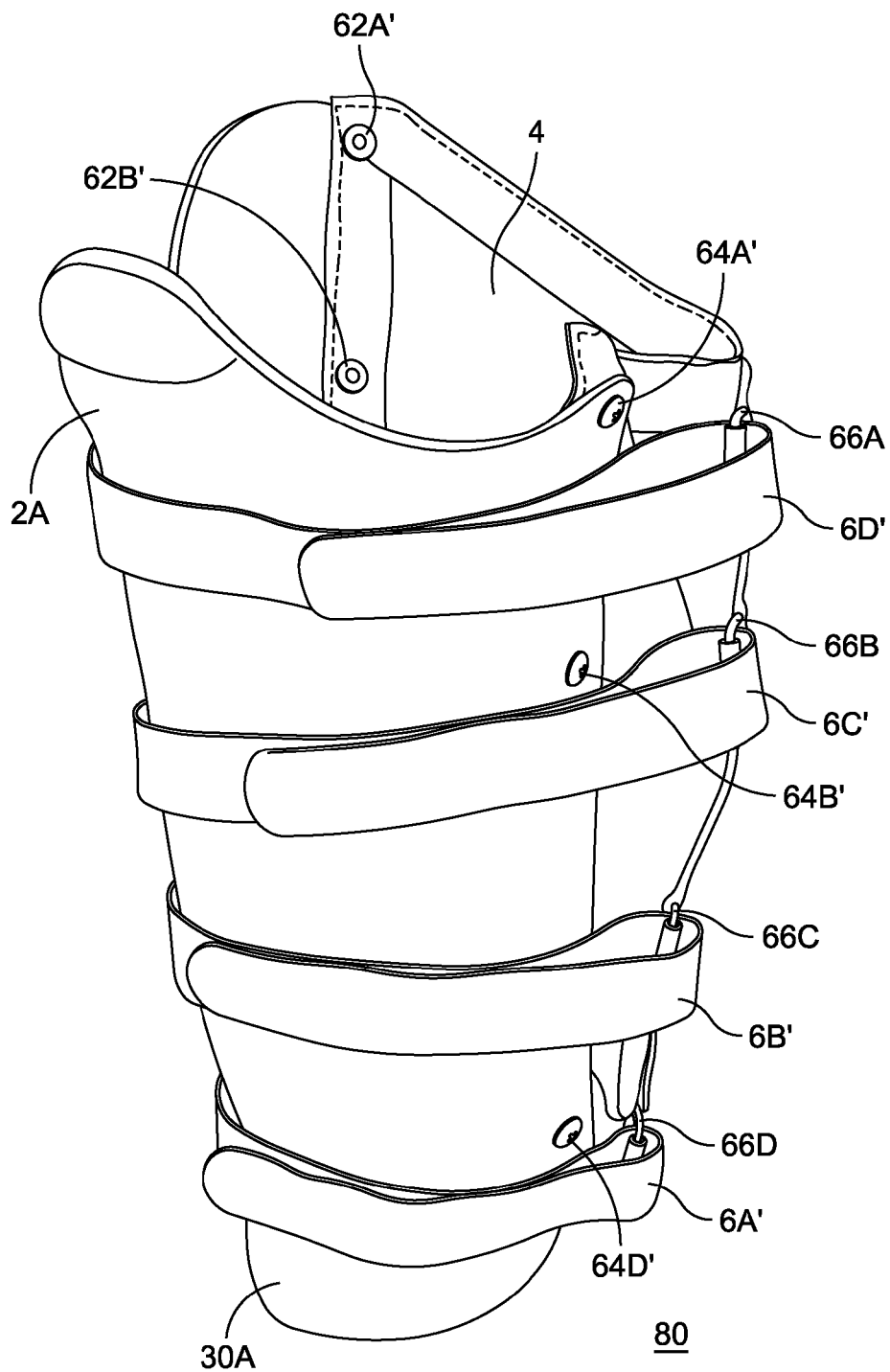
FIG. 6A is a schematic showing a posterior view of the rigid support of the transfemoral anterior sail socket of the present invention with the anterior flexible support and adjustment means.
Figure 6B:
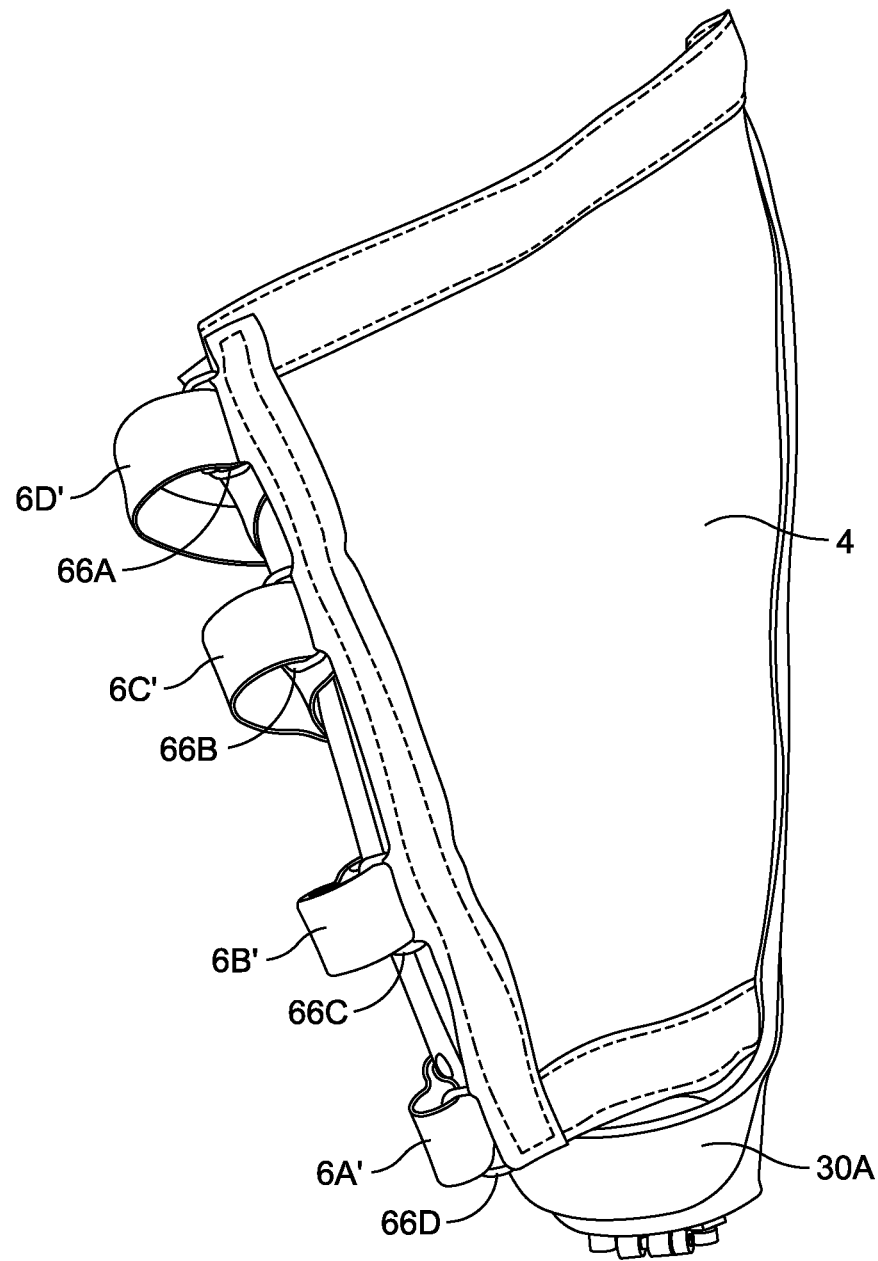
FIG. 6B is a schematic showing an anterior view of the rigid support of the transfemoral anterior sail socket of the present invention with the anterior flexible support and adjustment means.
Figure 7:
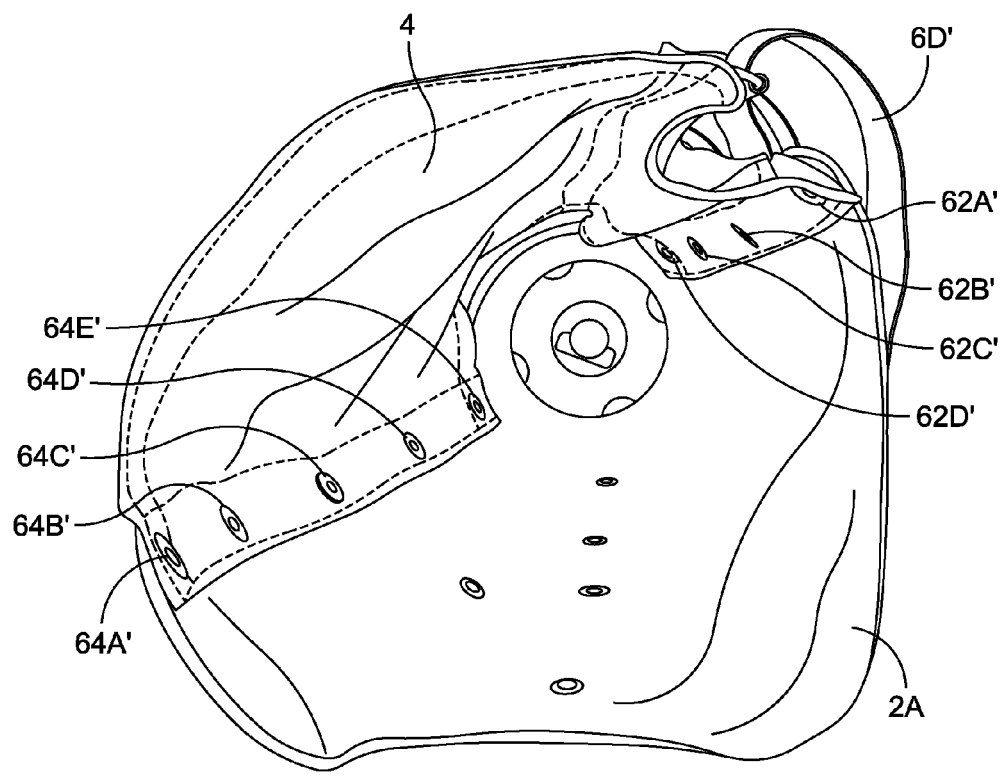
FIG. 7 is a schematic showing a top view of the transfemoral anterior sail socket of the present invention with the anterior flexible support and adjustment means.

FIGS. 6A, 6B and 7 show the transfemoral anterior sail socket system 80. Socket system 80 includes flexible support 4 and an adjustment means, which includes a set of rings 66A-66D and hook and loop fasteners, 6A$^1$, 6B$^1$, 6C$^1$ and 6D$^1$, as shown and described herein. Rigid support 2A has openings 68A-68E and 70A-70D through which grommets 64A$^1$-D$^1$ and 62A$^1$-D$^1$ are placed to secure sail 2A. See FIG. 7. The transfemoral anterior sail socket system works very similarly to the transfemoral posterior sail socket system, except it is modified so that the rigid support is on the posterior side and the sail is more on the anterior side.

Figure 8:
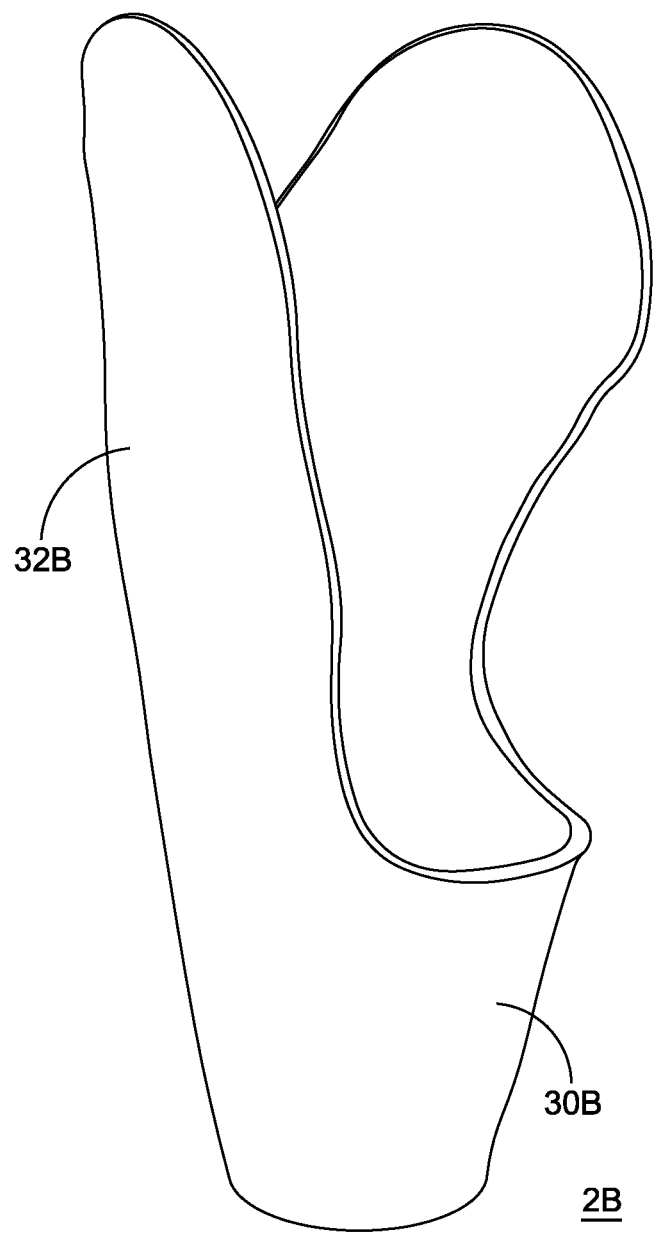
FIG. 8 is a schematic showing a perspective view of the rigid support (e.g., "J-socket") of the transtibial socket of the present invention without the flexible support (e.g., sail).
Figure 9A:
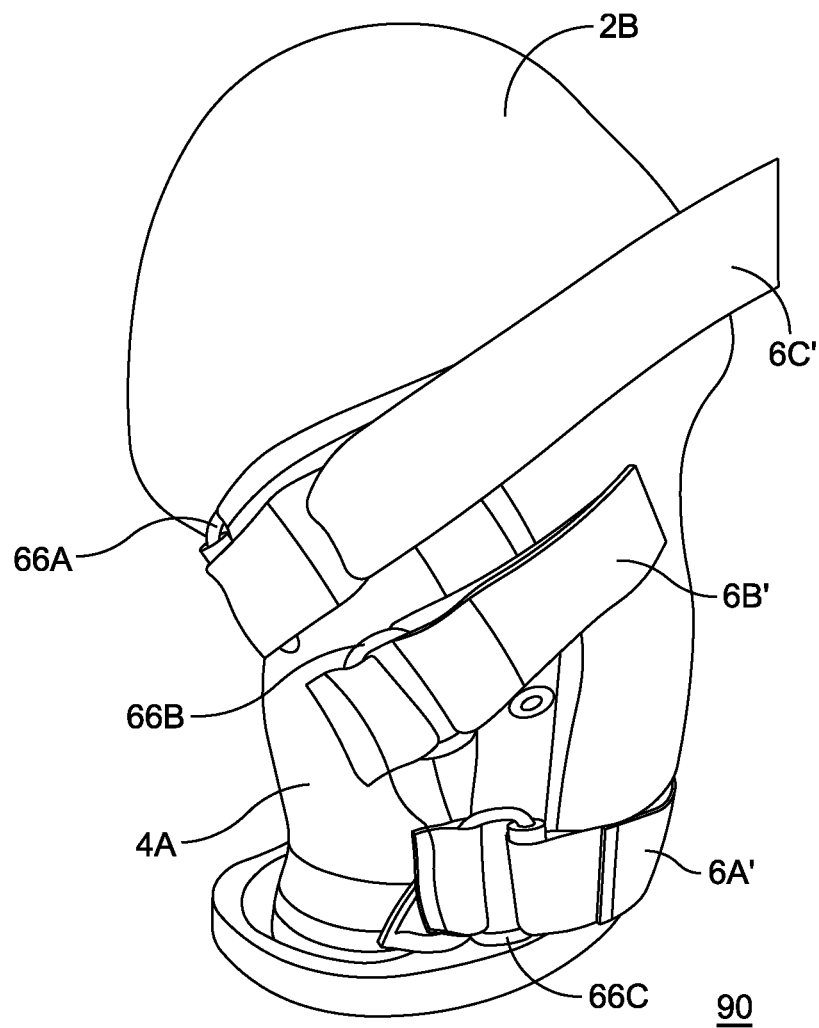
FIG. 9A is a schematic showing an anterior view of the rigid support of the transtibial socket of the present invention with the flexible support and adjustment means.
Figure 9B:
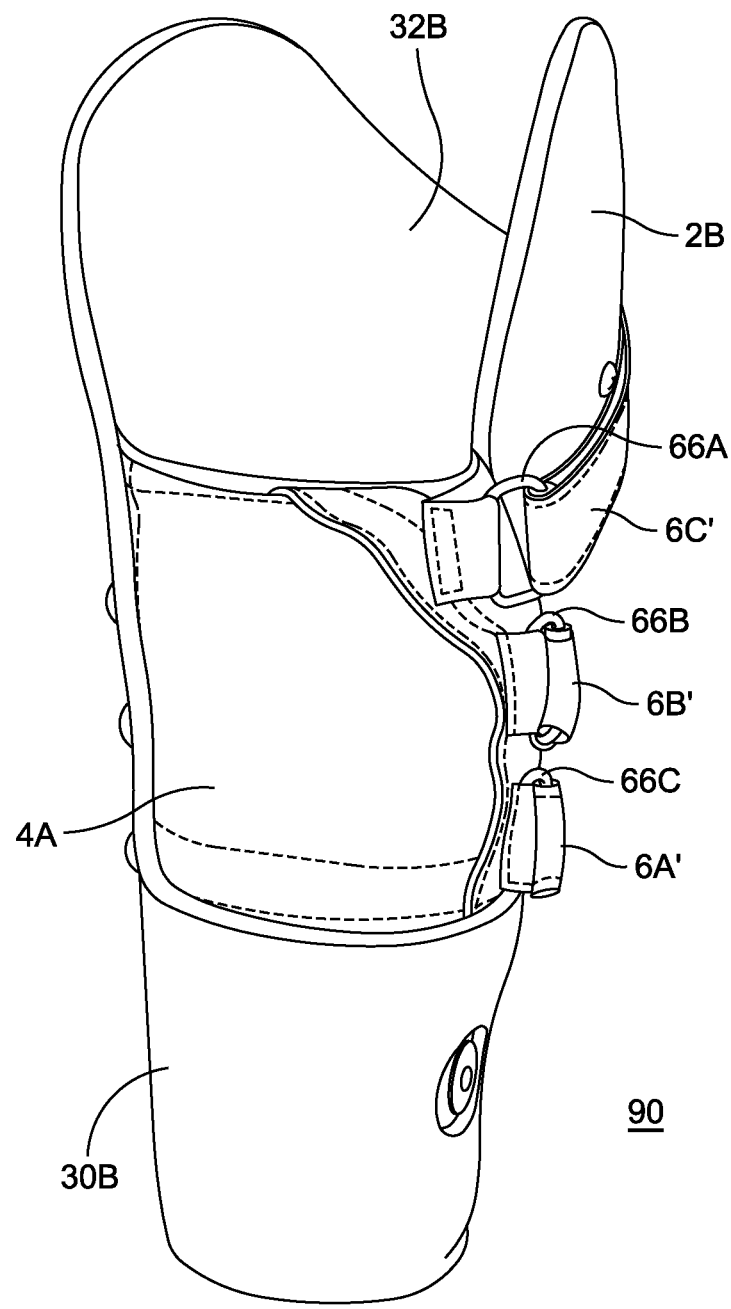
FIG. 9B is a schematic showing a posterior view of the rigid support of the transtibial socket of the present invention with the flexible support and adjustment means.
Figure 10:
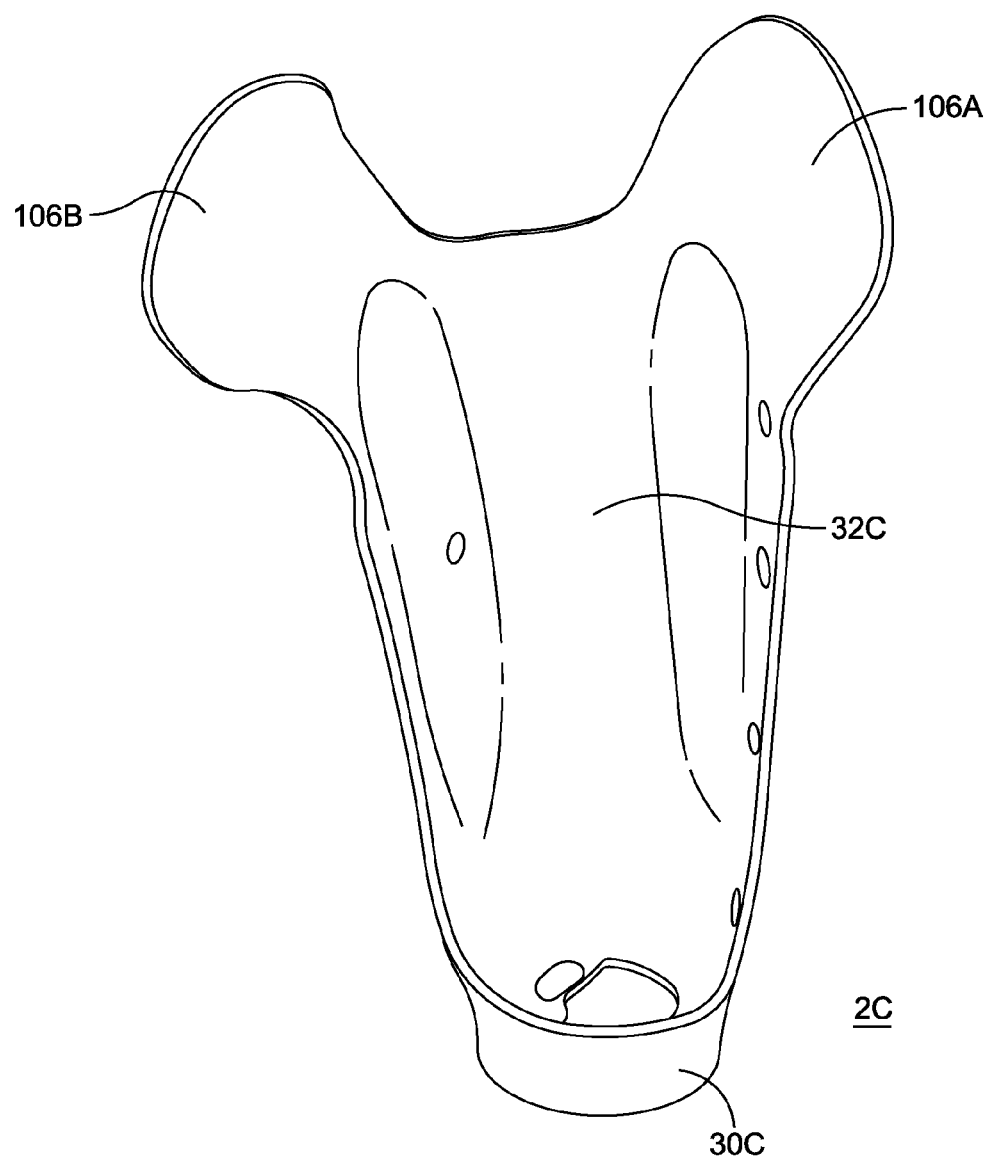
FIG. 10 is a schematic showing a perspective view of the rigid support (e.g., "J-socket") of the transhumeral socket of the present invention without the flexible support (e.g., sail).
Figure 11A:
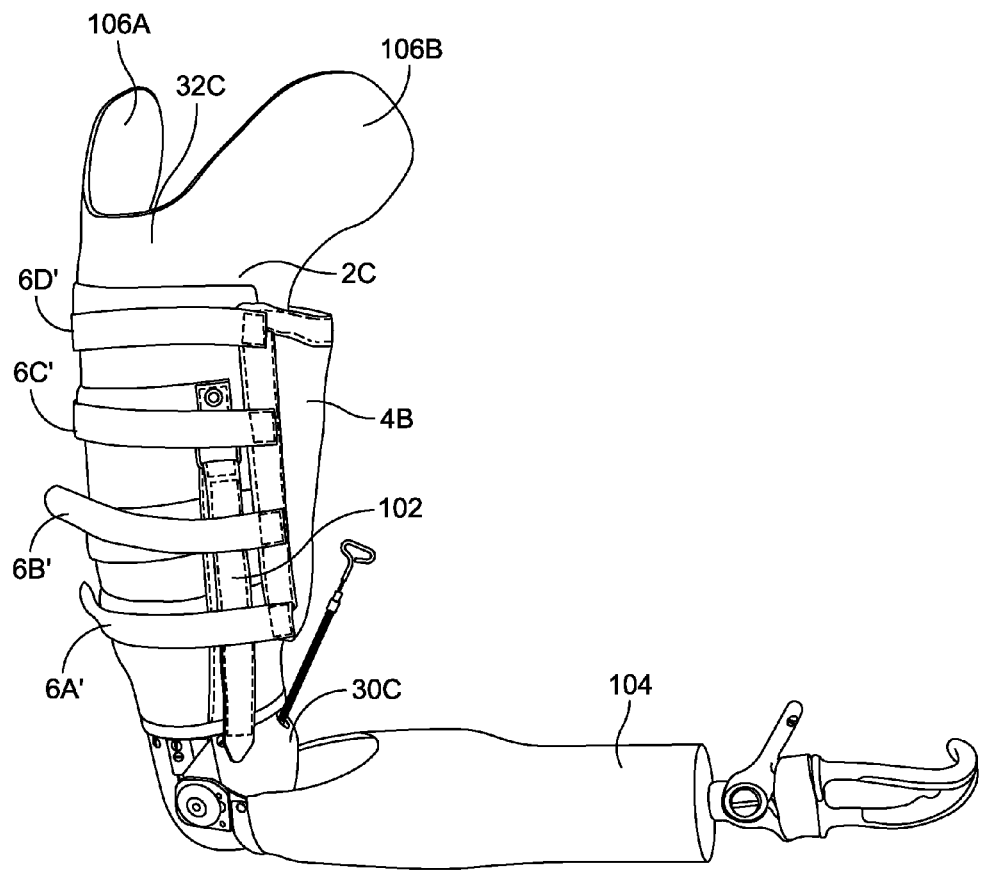
FIG. 11A is a schematic showing a lateral side view of the rigid support of the transhumeral socket of the present invention with the flexible support and adjustment means.
Figure 11B:
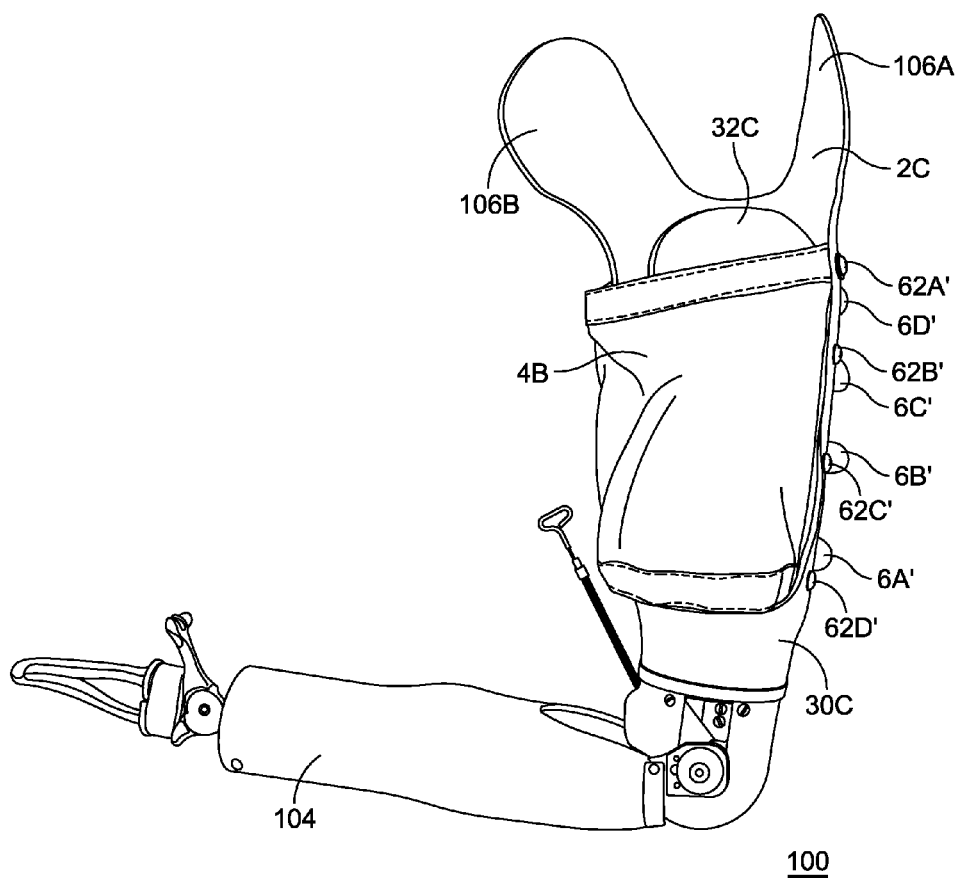
FIG. 11B is a schematic showing a medial side view of the rigid support of the transhumeral socket of the present invention with the flexible support and adjustment means.

FIGS. 8, 9A and 9B show the tibial socket system 90. Referring to FIG. 8, rigid support 2B is shown and also generally forms a "J" with base 30B and rigid member 32B. The J-socket is shaped as a partial socket to form essentially a "J" shape. Rigid support has rounded extension to conform to the knee to allow it to bend. The sail is adapted to fit the limb and has three fasteners, fasteners 6A$^1$, 6B$^1$, and 6C$^1$, and three rings, 66A-C. Socket system 90 has the elements described herein but adapted to fit a transtibial residual limb.

FIGS. 10, 11A, 11B and 12 show transhumeral socket system 100 used for amputations at the humerus. Rigid support 2C, also in the form of a "J" has base 30C and rigid member 32C. Rigid support 2C further includes wings 106A and 106B to provide additional stabilization of the prosthesis. As described herein the rigid support can be extended or modified to suit the type of amputation or characteristics of the residual limb.

Flexible support 4B of the transhumeral socket system can also be modified to for a humeral residual limb. In this embodiment, an anchor, strap 102, was added to provide additional support. As described herein, the sail provides circumferential forces when secured to the limb, but vertical or proximal/distal forces can additionally be applied with use of anchors. Such anchors can also be used to further secure the prosthesis to the socket system of the present invention. In this case, prosthesis 104 is attached to socket system 100.

Figure 12:
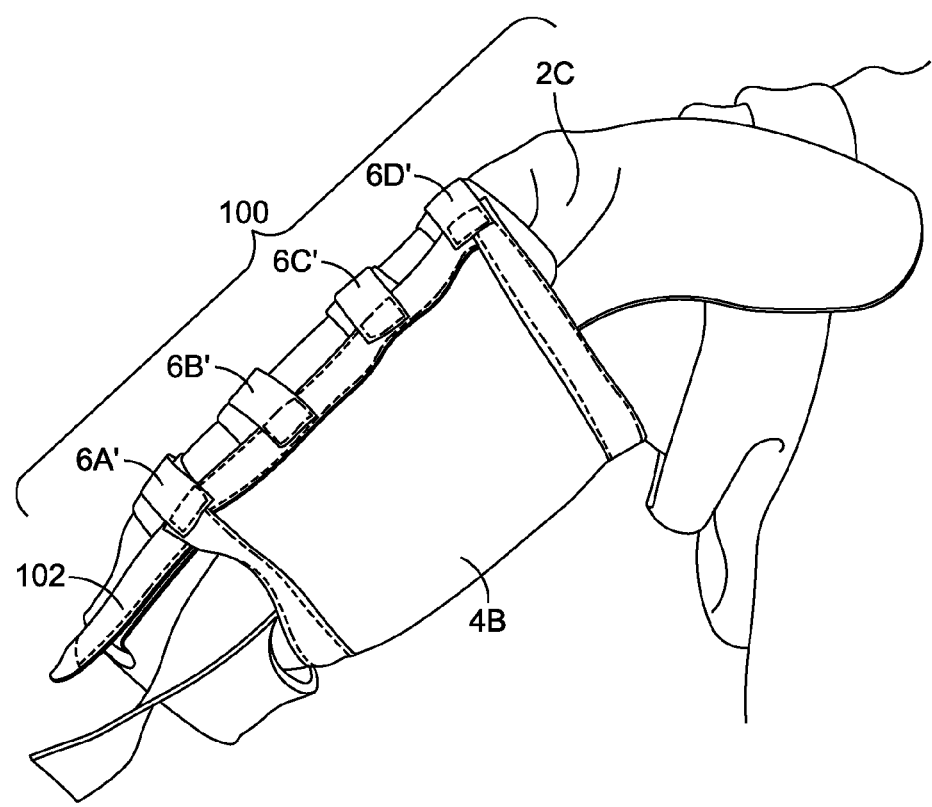
FIG. 12 is a schematic showing a side view of the rigid support of the transhumeral socket of the present invention with the flexible support and adjustment means on an individual.

FIG. 12 shows an advantage of the present invention. Flexible support 4B is secured such that the flexible support is snug against the arm pit. The individual enjoys a significant range of motion and additional comfort. Using a flexible support in this area, as compared to traditional sockets having a rigid support in this area, allows for this advantage.

Figure 13A:
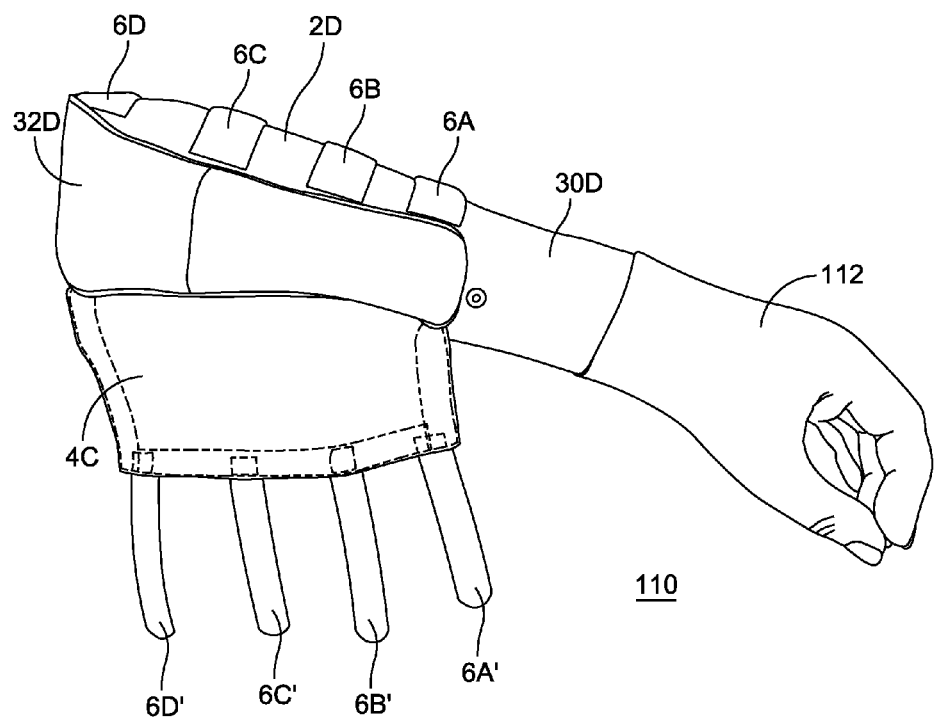
FIG. 13A is a schematic showing a perspective view of the rigid support of the transradial socket of the present invention with the flexible support and adjustment means in an open position.
Figure 13B:
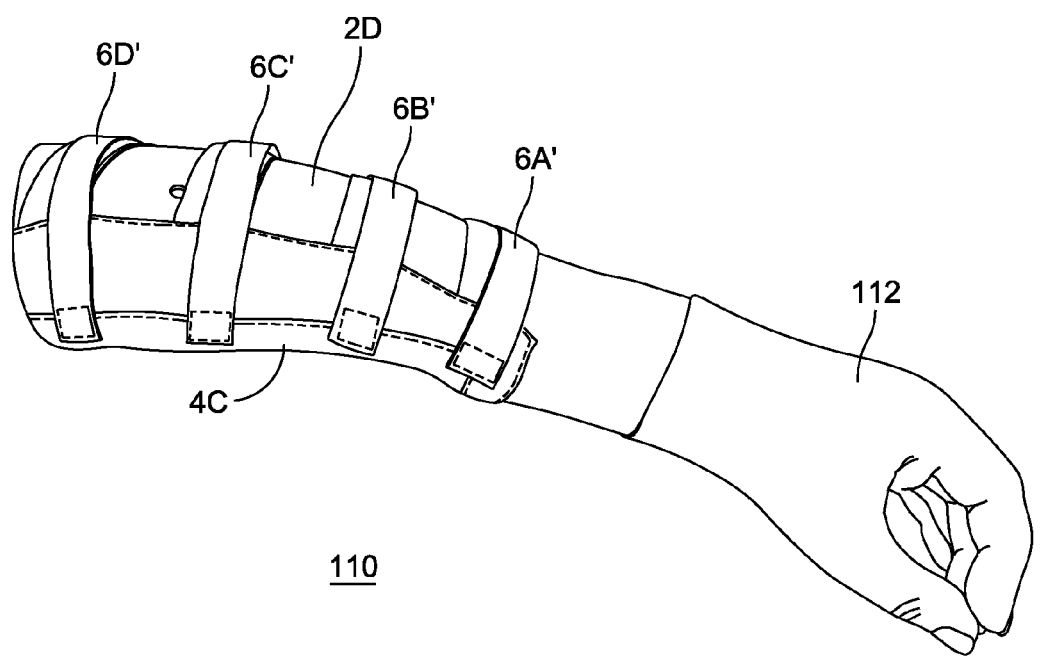
FIG. 13B is a schematic showing a perspective view of the rigid support of the transradial socket of the present invention with the flexible support and adjustment means in a closed position.
Figure 14:
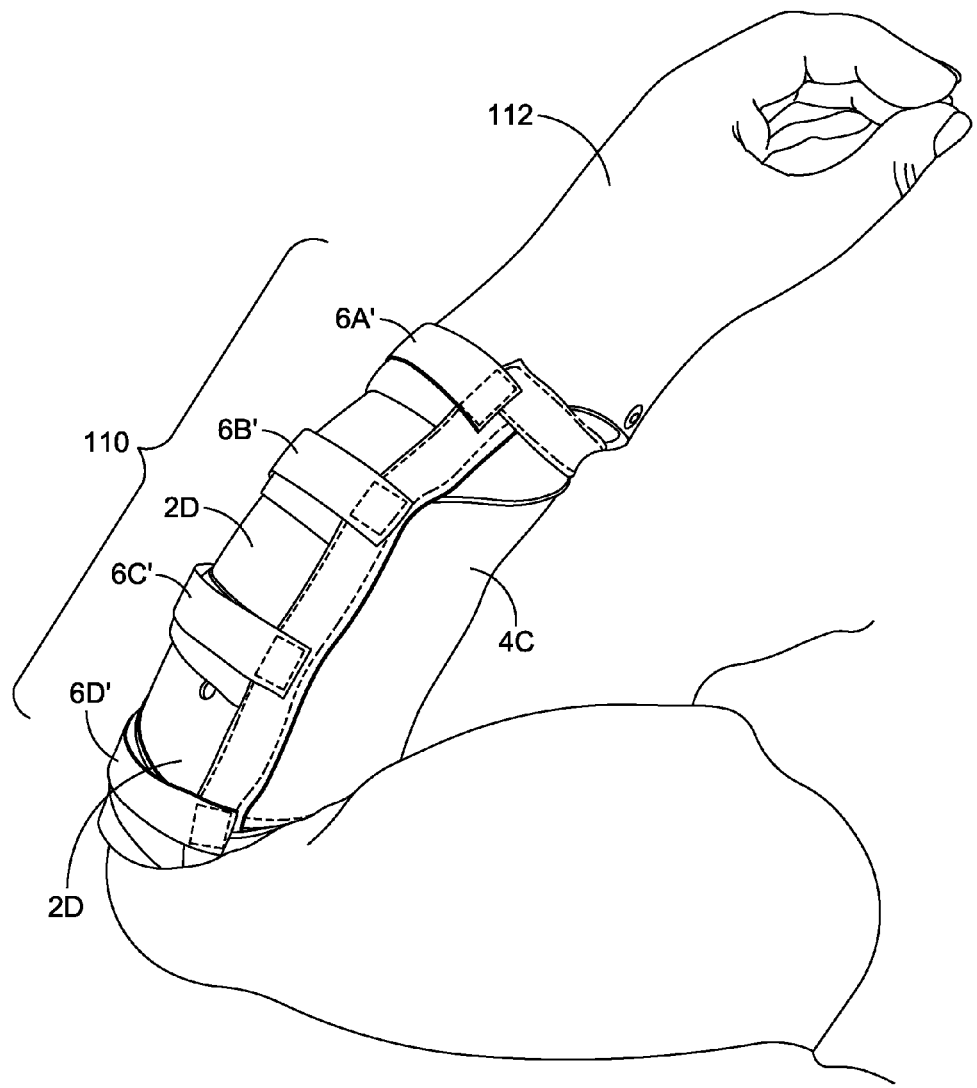
FIG. 14 is a schematic showing a perspective view of the rigid support of the transradial socket of the present invention with the flexible support and adjustment means on an individual whose arm is in a flexed position.

FIGS. 13A, 13B and 14 depict transradial socket system 110 of the present invention. FIG. 13 shows rigid support 2D having base 30D and rigid member 32D, forming generally a "J" shape. Attached to rigid support 2D is prosthesis 112. Flexible support 4C is adapted to fit the residual limb and rigid support 2D. It is slightly smaller in size than the sail used for the transfemoral socket systems. Flexible support 4C, like the flexible supports described herein, has an adjustment means which includes hook (i.e., fasteners 6A, 6B, 6C, and 6D) and loop fasteners, fasteners 6A$^1$, 6B$^1$, 6C$^1$, and 6D$^1$.

FIG. 14 shows the unprecedented flexibility of the socket system of the present invention in which the individual can flex his elbow with a significant range of motion with greater comfort than traditional sockets.

Other optional features of the socket of the present invention include a vacuum port (not shown) and one or more gel liners. To put the socket on an individual, the individual often begins by covering the residual limb with a gel liner, also referred to as an inner gel liner. A gel liner is a flexible, soft covering that is made from various materials such as a thermoplastic elastomer gel, urethane, silicon, and can be encased by or imbedded into fabric. The gel liner is intended to distribute pressure along the residual limb and reduce friction. Gel liners are commercially available e.g., from Ohio Willow Wood, Mt. Sterling, Ohio, Alpha Liner Model Nos. L-5681, or Ossur, Iceland, Iceross liner. The gel liner is largely for skin protection and comfort, but can also be used to vacuum seal the socket to the residual limb or to mechanically suspend the prosthesis via a mechanical lock (see FIG. 6B). Use of the gel liners and vacuum are optional, but can be used in certain embodiments preferred to provide better fit of the socket.

The socket system of the present invention, in an aspect, is then secured to the residual limb having the inner gel liner previously placed on the individual. The socket system of the present invention is secured using the adjustment means, as described herein. Once secured, gel liner 25, a second gel liner can be pulled up over the socket. The inner gel liner (not shown) folds down over the superior or top end of the socket to meet the second gel liner. The two gel liners overlap one another so that a seal can be created. A vacuum suction, which is optional, can be applied using the vacuum port and air between line liners can be removed and a seal is formed. The vacuum seal further assists securing the socket to the residual limb, but in certain embodiments, is not necessary if the closure system provides a good fit.

Accordingly, the present invention relates to a method of securing the socket to an individual. The method involves attaching an inner gel liner to the residual limb, securing the socket of the present invention to the residual limb, covering the secured socket with a second liner such that the second liner meets the inner liner, and vacuum sealing the liners and socket assembly.

In yet another embodiment, an inner gel liner with a locking mechanism at the distal end can be used. The locking mechanism (not shown), for example, can be a pin or a lanyard. Base 30 of rigid support 2 can have a locking mechanism to receive the pin and/or lanyard, to thereby secure the inner liner to the socket and suspend the limb. The locking mechanism has an arm to engage the lock. Examples of locking mechanism include shuttle locks, ratchet lock, lanyard strap, pin, SUMMIT brand Lock and the like. Locking liners that engage the locking mechanism are commercially available e.g., as Contexgel lock or Alpha unit.

The socket of the present invention further includes an attachment at the base so that the prosthetic can be secured to the socket. The attachment can be any attachment so long as the prosthetic device can be secured to the socket. In an embodiment, a four hole pattern endoskeletal attachment plate or a three pronged plate can be used. The attachment can also utilize a locking assembly (See U.S. Pat. No. 6,589,289), screws, plates, nuts, bolts, and the like.

When the socket of the present invention is used by an individual, the design of the socket allows for adjustment of volumetric changes in the residual limb. Reduction in rigidity coupled with a strong, but flexible support allows increased comfort as well as for the ability to adjust the circumferential forces to the residual limb and maintain proper socket fit and function. The adjustment means can be adjusted throughout the day by the individual, as desired. If toward the end of the day, the volume of residual limb of the individual shrinks a bit, then the individual can simply tighten the closure and adjust the circumference of the socket to compensate for the volume loss. Conversely, if the volume of the residual limb increases, then the individual can simply loosen the closure and increase the circumference of the socket to again compensate and maintain proper socket fit and function. Accordingly, the present invention includes methods of using (e.g., as when one is walking, or lifting) the socket described herein, and/or adjusting (e.g., tightening or loosening) the adjustment means to accommodate for volumetric changes in the residual limb.

The specific method of making the socket of present invention is described in the Exemplification. In general, the method of making the socket described herein involves selecting an individual with an amputation. A patient is selected if medically appropriate, healed, motivated, and the individual has sufficient bone length and soft tissue coverage in the residual limb to withstand the socket forces.

The actual measurement of the bone length is obtained with a soft measuring tape or measuring stick can be used. The bone length should be at least 10% (20%, 20%, 30%, 40%, or 50%) of the original femoral, tibial, radial or humeral length or greater. Soft tissue coverage is determined by palpating the soft tissue to assess for pressure sensitive areas (e.g., scars, skin graft, neuroma, or fistulas).

The patient can also be assessed to determine if he has a proper strength and range of motion in order to use a prosthetic device. Such an assessment is known in the art.

Measurements of the residual limb are also taken. In particular, measurements for a roll-on gel liner/interface can be taken with tape measure. Beginning about 4 cm from distal limb, the circumference of the residual limb can be determined. Measurements after the gel liner is applied are also taken. Typical measurements include circumference at various points, length of the residual limb from certain points of the body, and the like. Procedures for measuring for a traditional limb can be used including the use of scanners for three dimensional modeling (e.g., CAD CAM).

After measurements are taken, an impression of the residual limb is obtained. A positive model or mold is made from the impression in a traditional manner. The positive model or mold, is then modified by hand or CAD to achieve the proper size and shape. Transfemoral patients are generally casted in a standing position if possible, with plaster. Various types of casting materials can be used, including plaster of Paris, synthetics such as fiberglass, or conformable synthetic plasters such as J&J's conformable or Delta light synthetic. The plaster hardens after a few minutes.

Test sockets were molded over the modified models and then cut and trimmed and finished. The rigid support can be made from any material that can be molded to conform to the shape and contours of the residual limb, and hardens. The rigid support was made with standard prosthetic materials. Polypropylene and similar thermoplastics were used to fabricate initial sockets and acrylic resins are used to laminate fiberglass, nylon and carbon materials to make definitive socket components. The rigid support can also be made from co-polymers, modified epoxy acrylics, polyester or epoxy resins and the like. Epoxy can layered with nylon, carbon braids or fiberglass cloths. Additional moldable materials that harden and are suitable for making the rigid support are known in the art, or can be developed in the future.

In an embodiment, the flexible support or garment is made of a non-elastic material such as ripstop nylon or CONDURA fabric, and incorporates various closures. The garments were custom made to fit or go over the socket and positive plaster model. The closure is sewn and installed as part of the garment construction. The garment is cut and sewn to fit the individual, and adjust for volumetric changes during use. These closures, as described herein, are constructed of various materials including laces, ties, hook and loop straps, metal loops or roller loops, draw strings pulled through modified block and tackle type compound closures. The closures are secured to the rigid support, to the flexible support or both. In an embodiment, socket attachment blocks using a standard 4 hole pattern were aligned and incorporated into the sockets.

After the rigid support and garment are made, the rigid support is attached to the appropriate prosthetic components i.e. knees, shins, ankles, feet, hands, wrists for ambulation/use trials. Once the alignment and socket design are deemed satisfactory the limb is finished using traditional fabrication techniques.

Exemplification

The device shown in all of the figures were made. The following described the specific process used for making the transfemoral posterior sail socket system, but the process was adapted to fit other types of socket systems including the transfemoral anterior sail socket system, the transtibial socket system, the transhumeral socket system and the radial socket system.

The patient was evaluated for a prosthesis. The patient was assessed and determined to have adequate general health, motivation, and sufficient bone length and soft tissue coverage to withstand the socket forces. The patient was also assessed and determined that he does have adequate strength and proper range of motion in order to use a prosthetic device.

Measurements of the limb were then taken. In particular, measurements for a roll-on gel liner/interface were taken with tape measure. Beginning 4 cm from distal limb, the circumference of the residual limb was obtained. A gel liner from Ossur Americas (Foot Hill Ranch, Calif.) was obtained. Measurements after the gel line was applied were also taken using standard procedures.

The limb was then prepared for casting with elastic casting garment (Tubigrip from Molnlycke Health Care) and a separator bag from ischial tubrosity to the distal femur. The elastic casting garment functions to pre-compress the soft tissue and length of the residual limb. The garment is held in place with elastic straps.

The patient was casted in a standing position if possible, with plaster. In this case, plaster of Paris was used, but other synthetic casting materials can be used.

After the plaster hardens, the cast was inspected to ensure that there was a good conforming shape both anteriorly and laterally, and that adequate relief for distal lateral femur was present.

Negative mold powdered such as talcum powder was used, and the mold was sealed and filled with dental plaster. A 1" mandrill was inserted, maintaining normal alignment. The model was then rectified by hand to smooth and create necessary contours anteriorly and laterally.

A test socket was then made from ¼ inch PETG (Polyethylene Terephthalate formulation marketed under the trade mark VIVAK). The socket was cut out and trimmed. In particular, the socket was trimmed beginning from the anterior side. The socket trim line was established just posterior to the adductor longus tendon origin and then inferiorly to a point approximately 2 inches proximal to the distal end, then extending posteriorly (roughly 180°) and then proximally to posterior lateral apex (just posterior to the Greater Trochanter in the wallet hollow).

A four hole pattern endoskeletal attachment plate is attached to the test socket but others can be used such as a three pronged plate.

The flexible support or garment was fabricated for use in the socket design shown it the figures. The width of the garment was determined by tapeline measurements taken with the test socket placed on the positive plaster mold from the proximal posterior lateral socket trim line to proximal anterior medial socket trim line. The length of the garment was measured from the gluteal fold to bottom of the socket trim line. A paper pattern was made to verify the measurements and facilitate the garment fabrication.

A soft strap was sewn into the proximal end of the garment to create a comfortable radius and to follow the anatomical contours (e.g., the gluteal fold, to hamstring origin under the ischial tuberosity following the ischial ramus complex to the adductor longus). The garment was attached with rivets to the posterior lateral trim line of the rigid support.

Three to six metal loops are attached to the anterior medial end of garment and corresponding loops are attached to anterior portion of the rigid support. The closure can be made from webbing straps (e.g., DACRON® webbing) with hook and loop fasteners.

A locking gel liner was applied to the residual limb and attached to the socket.

The socket shown in figures was aligned and fine tuned after watching how the patient walked in the socket.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A socket system for attachment of a prosthetic device to a residual limb of an individual, the residual limb having a volume, a surface area, and a length defined between a proximal end and a distal end along a longitudinal axis, wherein the socket system comprises:
   a. a rigid support, the rigid support having a rigid member and a distal base, wherein the rigid member is configured to extend along the length of the residual limb, and wherein the rigid member is shaped to conform to between about 15% and about 75% of the surface area of the residual limb, to thereby define, when in use, a balance of the surface area of the residual limb unsupported by the rigid member;
   b. a non-elastic, non-rigid, flexible support made from one or more materials used to make wearable garments, wherein the non-elastic, non-rigid, flexible support is fixedly secured along its length to the rigid support and positioned, when in use, to cover the balance of the surface area of the residual limb unsupported by the rigid member, wherein the rigid member and the non-elastic, non-rigid, flexible support are configured to cover opposing sides along the longitudinal axis of the residual limb, and wherein the rigid member and the non-elastic, non-rigid, flexible support do not overlap except in areas used to secure one to the other; and
   c. an adjuster to maintain a volumetric fit of the socket system to the residual limb, wherein the adjuster is directly attached to each of the rigid support and the non-elastic, non-rigid, flexible support;
wherein, when in use, the socket system maintains hydrostatic weight bearing while the volume of the residual limb changes.

2. The socket system of claim 1, further comprising an attachment for the prosthetic device, wherein the attachment is at the distal base of the rigid support.

3. The socket system of claim 1, wherein the rigid member is shaped to conform to at least about 50% of the surface area of the residual limb.

4. The socket system of claim 1, wherein the rigid member is shaped to cover at least about 180° of a circumference of the residual limb.

5. The socket system of claim 1, wherein the adjuster is selected from the group consisting of: fasteners, straps, snaps, buckles, buttons, hooks, elastic members, trap-locks, ties, laces, clips, zippers, metal loops or roller loops, drawstring & cord lock arrangements, hook-to-hook arrangements, hook & loop arrangements, bungee cord & cord lock arrangements, magnets, slides, block and tackle arrangements, rope/chord and hook arrangements, and a combination thereof.

6. The socket system of claim 1, further comprising a first gel liner, a second liner, a locking mechanism, or a combination thereof.

7. The socket system of claim 1, further comprising a vacuum port, suction valve or a locking mechanism.

8. The socket system of claim 1, wherein the socket system is configured to fit the residual limb, wherein the residual limb is a transfemoral residual limb, a transtibial residual limb, a transhumeral residual limb, or a transradial residual limb.

9. The socket system of claim 1, wherein the non-elastic, non-rigid, flexible support is configured to cover a posterior side of a transfemoral residual limb.

10. The socket system of claim 1, wherein the non-elastic, non-rigid, flexible support is configured to cover a posterior side of a transtibial residual limb.

11. The socket system of claim 1, wherein the non-elastic, non-rigid, flexible support is configured to cover a medial side of a transhumeral residual limb.

12. The socket system of claim 1, wherein the non-elastic, non-rigid, flexible support is configured to cover a radial side of a transradial residual limb.

13. A socket for attachment of a prosthetic device to a residual limb of an individual, the residual limb having a circumference, a volume, a surface area, and a length defined between a proximal end and a distal end along a longitudinal axis, wherein the socket comprises:
   a. a rigid support, wherein the rigid support comprises a distal base and a rigid member that is shaped to conform to at least a portion of the residual limb, wherein the rigid member is configured to extend along the length of the residual limb, and wherein the rigid member is configured to cover at least about 180° of the circumference of the residual limb, thereby leaving a balance of the surface area of the residual limb unsupported by the rigid member;
   b. a non-elastic, non-rigid, flexible support made from one or more materials used to make wearable garments, wherein the non-elastic, non-rigid, flexible support is fixedly secured along its length to the rigid support, wherein the flexible support covers the balance of the residual limb, wherein the rigid member and the non-elastic, non-rigid, flexible support are configured to independently cover opposing sides along the longitudinal axis of the residual limb, and wherein the rigid member and the non-elastic, non-rigid, flexible support do not overlap except in areas used to secure one to the other; and
   c. an adjuster to maintain a volumetric fit of the socket to the residual limb when in use, wherein the adjuster is directly attached to each of the rigid support and the non-rigid, flexible support;
wherein, when in use, the socket adjusts to fit the volume of the residual limb and wherein, when in use, the socket provides hydrostatic weight bearing.

14. The socket of claim 13, further comprising an attachment for the prosthetic device, wherein the attachment is at the distal base of the rigid support.

15. The socket of claim 13, wherein the rigid member is shaped to conform to at least about 50% of the surface area of the residual limb.

16. The socket of claim 13, further comprising a first gel liner, a second liner, or a combination thereof.

17. The socket of claim 13, wherein the rigid support is made from a material that comprises thermoplastic, polypropylene, acrylic, polyester or epoxy resins layered with nylon, carbon braids or fiberglass cloths, or a combination thereof.

18. The socket kit of claim 13, further comprising a vacuum port.

19. The socket of claim 13, wherein the socket is configured to fit the residual limb wherein the residual limb is a transfemoral residual limb, a transtibial residual limb, a transhumeral residual limb, or a transradial residual limb.

20. The socket of claim 13, wherein the non-elastic, non-rigid, flexible support is configured to cover a posterior side of a transfemoral residual limb.

21. The socket of claim 13, wherein the non-elastic, non-rigid, flexible support is configured to cover a posterior side of a transtibial residual limb.

22. The socket of claim 13, wherein the non-elastic, non-rigid, flexible support is configured to cover a medial side of a transhumeral residual limb.

23. The socket of claim 13, wherein the non-elastic, non-rigid, flexible support is configured to cover a radial side of a transradial residual limb.

* * * * *